United States Patent
Ogawa (10) Patent No.: US 8,755,040 B2
(45) Date of Patent: Jun. 17, 2014

(54) ILLUMINATING APPARATUS, PATTERN INSPECTION APPARATUS, AND METHOD OF FORMING ILLUMINATING LIGHT

(75) Inventor: Riki Ogawa, Kanagawa (JP)

(73) Assignee: NuFlare Technology, Inc., Numazu-shi (JP)

( * ) Notice: Subject to any disclaimer, the term of this patent is extended or adjusted under 35 U.S.C. 154(b) by 125 days.

(21) Appl. No.: 13/351,555

(22) Filed: Jan. 17, 2012

(65) Prior Publication Data

US 2012/0189032 A1    Jul. 26, 2012

(30) Foreign Application Priority Data

Jan. 20, 2011    (JP) ................... 2011-009677

(51) Int. Cl.
  *G01N 21/956*   (2006.01)
  *G01N 21/95*    (2006.01)

(52) U.S. Cl.
  CPC .......... *G01N 21/956* (2013.01); *G01N 21/9505* (2013.01)
  USPC ........ 356/237.2; 359/558; 362/259; 362/268; 362/269

(58) Field of Classification Search
  USPC ........................... 362/268, 331; 359/566–590; 356/237.2–237.6
  See application file for complete search history.

(56) References Cited

U.S. PATENT DOCUMENTS

| | | | | |
|---|---|---|---|---|
| 6,594,090 | B2 * | 7/2003 | Kruschwitz et al. | 359/707 |
| 6,898,216 | B1 * | 5/2005 | Kleinschmidt | 372/9 |
| 7,515,248 | B2 * | 4/2009 | Tanitsu et al. | 355/71 |
| 7,649,625 | B2 * | 1/2010 | Takada | 356/237.5 |
| 7,955,765 | B2 * | 6/2011 | Shinoda | 430/30 |
| 2002/0001759 | A1 * | 1/2002 | Ohashi et al. | 430/5 |
| 2012/0242961 | A1 * | 9/2012 | Miura | 353/38 |

FOREIGN PATENT DOCUMENTS

JP    11-72905    3/1999

* cited by examiner

*Primary Examiner* — Diane Lee
*Assistant Examiner* — Gerald J Sufleta, II
(74) *Attorney, Agent, or Firm* — Oblon, Spivak, McClelland, Maier & Neustadt, L.L.P.

(57) ABSTRACT

An illuminating apparatus includes a rotating phase plate having a height equal to or less than a wavelength of light from a light source and including a plurality of randomly arranged step regions so as to change a phase of light from the light source by allowing the light beam to pass therethrough; and a fly's eye lens including an array of a plurality of lenses configured to pass the light beam passed through the rotating phase plate, wherein a portion in which a product of a maximum size of the plurality of step regions and an optical magnification from the rotating phase plate to a plane of incidence of the fly's eye lens is equal to or less than an arrangement pitch of the plurality of lenses and a portion in which the product is larger than the arrangement pitch of the plurality of lenses are mixed.

10 Claims, 9 Drawing Sheets

ILLUMINATING APPARATUS, PATTERN INSPECTION APPARATUS, AND METHOD OF FORMING ILLUMINATING LIGHT

CROSS-REFERENCE TO RELATED APPLICATION

This application is based upon and claims the benefit of priority from prior Japanese Patent Application No. 2011-009677 filed on Jan. 20, 2011 in Japan, the entire contents of which are incorporated herein by reference.

BACKGROUND OF THE INVENTION

1. Field of the Invention

The present invention relates to an illuminating apparatus, a pattern inspection apparatus, and a method of forming illuminating light, and for example, relates to an illuminating apparatus that reduces coherence of coherent light, a pattern inspection apparatus that inspects an object to be a target object used for fabricating a semiconductor for pattern defects by using illuminating light of such an apparatus, and a method of forming the illuminating light.

2. Related Art

In recent years, with increasingly higher integration and larger capacity of LSIs, the line width of a circuit demanded for semiconductor devices is becoming increasingly narrower. Such semiconductor devices are fabricated by exposing and transferring a pattern onto a wafer using a reduced projection aligner, a so-called stepper, to form a circuit using an original pattern (also called a mask or reticle) on which a circuit pattern is formed. Thus, for the fabrication of a mask to transfer such a fine circuit pattern onto a wafer, a pattern writing apparatus capable of writing a fine circuit pattern is used. By using such a pattern writing apparatus, a pattern circuit may directly be written onto the wafer. For example, an electron beam or laser beam is used to write a pattern.

In addition, improving yields is indispensable for fabrication of LSIs requiring huge fabrication costs. However, patterns forming an LSI are moving, as is typically observed in a DRAM (random access memory) of 1 gigabit or so, from a submicron to the order of nanometer. As a major factor that reduces yields, pattern defects of a mask used when a hyperfine pattern is exposed and transferred onto a semiconductor wafer by photolithography technology can be cited. In recent years, with increasingly finer LSI dimensions of patterns formed on a semiconductor wafer, dimensions that need to be detected as a pattern defect have become extremely small. Thus, a pattern inspection apparatus that inspects a transfer mask used for LSI fabrication for defects needs to be more precise.

On the other hand, with the development of multimedia, liquid crystal displays (LCDs) have an increasingly larger liquid crystal substrate size of 500 mm×600 mm or more and finer patterns such as thin film transistor (TFT) formed on the liquid crystal substrate. Thus, inspection for extremely small pattern defects in a wide range is increasingly required. Therefore, development of a pattern inspection apparatus that inspects a photomask used for fabricating such a large-area LCD pattern and a large-area LCD for defects efficiently in a short time is also urgently needed.

With increasingly finer mask patterns and higher integration, higher resolution is required from an inspection apparatus and the wavelength of illuminating light of the inspection apparatus becomes shorter. For example, deep ultraviolet light with a wavelength of 266 nm or less is used. Such illuminating light is oscillated from a laser light source apparatus. However, laser light emitted from such a laser light source is a coherent light, causing a problem in that certain interference fringes (speckles) arise due to coherence. Thus, attempts are made to eliminate coherence by, for example, passing a light beam from a light source through a fly's eye lens and further passing the passed light beam through a rotating phase plate (see, for example, Japanese Patent Application Laid-Open No. 11-72905).

As described above, attempts to eliminate coherence of coherent light have been made, but no technique to adequately solve the problem has been established.

BRIEF SUMMARY OF THE INVENTION

In accordance with one aspect of the present invention, an illuminating apparatus, includes:
a light source configured to generate coherent light;
a rotating phase plate in which a plurality of step regions is arranged randomly and has a height equal to or less than a wavelength of the light, and configured to change a phase of a light beam from the light source by allowing the light beam to pass therethrough; and
a fly's eye lens in which a plurality of lenses is arranged like an array and configured to allow the light beam having passed through the rotating phase plate to pass,
wherein a portion in which a product of a maximum size of the plurality of step regions and an optical magnification from the rotating phase plate to a plane of incidence of the fly's eye lens is equal to or less than an arrangement pitch of the plurality of lenses, a portion in which the product is larger than the arrangement pitch of the plurality of lenses are mixed, the maximum size of the plurality of step regions is a maximum width size on a surface of each step region perpendicular to a direction of an optical axis and the surface of each step region is formed in a same shape.

In accordance with another aspect of this invention, an illuminating apparatus, includes:
a light source configured to generate coherent light;
a rotating phase plate in which a plurality of step regions is arranged randomly and has a height equal to or less than a wavelength of the light, and configured to change a phase of a light beam from the light source by allowing the light beam to pass therethrough; and
a fly's eye lens in which a plurality of lenses is arranged like an array and configured to allow the light beam having passed through the rotating phase plate to pass,
wherein a portion in which a maximum size of the plurality of step regions is equal to or less than an arrangement pitch of the plurality of lenses, a portion in which the maximum size is larger than the arrangement pitch of the plurality of lenses are mixed, the maximum size of the plurality of step regions is a maximum width size on a surface of each step region perpendicular to a direction of an optical axis and the surface of each step region is formed in a same shape.

In accordance with a further aspect of the invention, an illuminating apparatus, includes:
a light source configured to generate coherent light;
a rotating phase plate in which a plurality of step regions is arranged randomly and has a height equal to or less than a wavelength, and configured to change a phase of a light beam from the light source by allowing the light beam to pass therethrough; and
a plurality of fly's eye lenses in which a plurality of lenses is arranged like an array, configured to have different arrangement positions from the rotating phase plate, and configured to allow the light beam having passed through the rotating phase plate to pass, wherein a portion in which a first product of a maximum size of the plurality of step regions and an optical magnification from the rotating phase plate to a plane of incidence of one of the fly's eye lenses is equal to or less than an arrangement pitch of the plurality of lenses of the one of the fly's eye lenses and a portion in which the first product is larger than the arrangement pitch of the plurality of lenses of the one of the fly's eye lens are mixed, and a portion in which where a second product of the maximum size of the plurality of step regions and the optical magnification from the rotating phase plate to the plane of incidence of the other of the fly's eye lenses is equal to or less than the arrangement pitch of the plurality of lenses of the other of the fly's eye lenses, a portion in which where the second product is larger than the arrangement pitch of the plurality of lenses of the other of the fly's eye lenses are mixed, the maximum size of the plurality of step regions is a maximum width size on a surface of each step region perpendicular to a direction of an optical axis and the surface of each step region is formed in a same shape.

In accordance with a further aspect of the invention, a pattern inspection apparatus, includes:

a light source configured to generate coherent light;

a rotating phase plate in which a plurality of step regions is arranged randomly and has a height equal to or less than a wavelength of the light, and configured to change a phase of a light beam from the light source by allowing the light beam to pass therethrough;

a fly's eye lens in which a plurality of lenses is arranged like an array and configured to allow the light beam having passed through the rotating phase plate to pass;

an optical image acquisition unit configured to acquire an optical image of a pattern by using the light beam having passed through the fly's eye lens as illuminating light and by illuminating a substrate on which the pattern is formed with the illuminating light; and a comparing unit configured to compare the optical image and a reference image, wherein a portion in which a product of a maximum size of the plurality of step regions and an optical magnification from the rotating phase plate to a plane of incidence of the fly's eye lens is equal to or less than an arrangement pitch of the plurality of lenses, a portion in which the product is larger than the arrangement pitch of the plurality of lenses are mixed, the maximum size of the plurality of step regions is a maximum width size on a surface of each step region perpendicular to a direction of an optical axis and the surface of each step region is formed in a same shape.

In accordance with a further aspect of the invention, a method of forming illuminating light, includes:

generating coherent light from a light source;

changing a phase of a light beam from the light source by causing a rotating phase plate that has a plurality of step regions arranged randomly and having a height equal to or less than a wavelength formed thereon to pass the light beam from the light source; and causing a fly's eye lens in which a plurality of lenses is arranged like an array to pass the light beam having passed through the rotating phase plate, wherein a relationship between the rotating phase plate and the fly's eye lens, is configured to mix a portion in which a product of a maximum size of the plurality of step regions and an optical magnification from the rotating phase plate to a plane of incidence of the fly's eye lens is equal to or less than an arrangement pitch of the plurality of lenses, a portion in which the product is larger than the arrangement pitch of the plurality of lenses, the maximum size of the plurality of step regions is a maximum width size on a surface of each step region perpendicular to a direction of an optical axis and the surface of each step region is formed in a same shape.

DETAILED DESCRIPTION OF THE INVENTION

In the embodiments below, an illuminating apparatus capable of eliminating coherence of coherent light, a pattern inspection apparatus, and a method will be described.

First Embodiment

Figure 1:
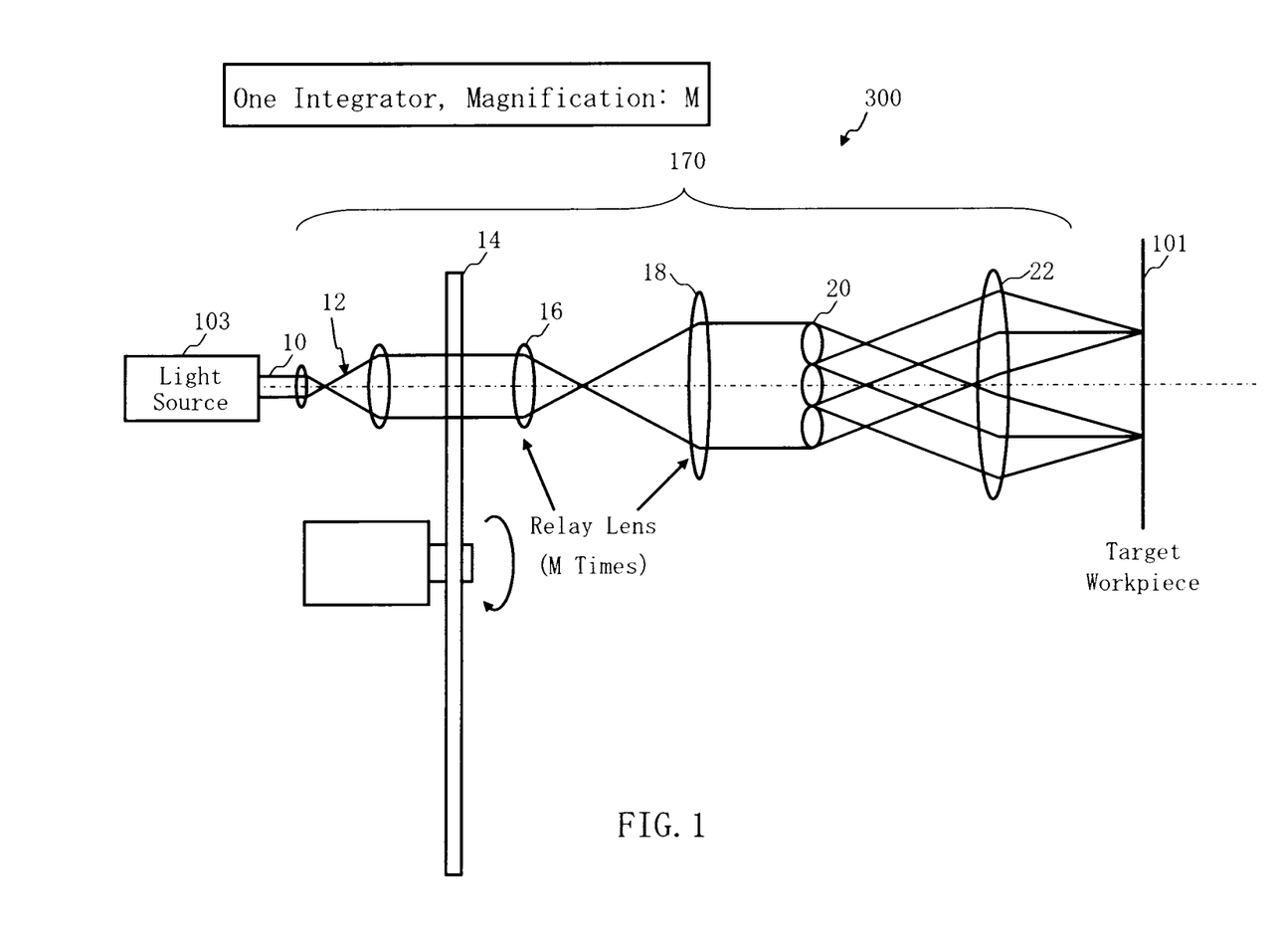
FIG. 1 is a conceptual diagram showing the configuration of an illuminating apparatus according to a first embodiment.

FIG. 1 is a conceptual diagram showing the configuration of an illuminating apparatus according to a first embodiment. In FIG. 1, an illuminating apparatus 300 includes a light source 103 and an illuminating optical system 170. The illuminating optical system 170 has a beam expander 12, a rotating phase plate 14, relay lenses 16, 18, an integrator (optical integrator: fly's eye lens) 20, and a condenser lens 22.

The light source 103 generates coherent light. For example, ultraviolet light with a wavelength of 266 nm is generated. A light beam 10 to be a coherent light emitted from the light source 103 is expanded by the beam expander 12 and caused to pass through the rotating phase plate 14 that rotates around a center axis thereof. Spatial coherency is reduced by causing the light beam 10 to pass through the rotating phase plate 14. Then, the optical magnification between the rotating phase plate 14 and the plane of incidence of the integrator 20 is adjusted to M times by the relay lenses 16, 18 arranged between the rotating phase plate 14 and the integrator 20. The light beam having passed through the rotating phase plate 14 and the relay lenses 16, 18 enters the integrator 20. Then, the light beam having passed through the integrator 20 is focused on a photomask 101 to be an object by the condenser lens 22 to illuminate the surface of the photomask 101 with the light beam.

Figures 2A, 2B:
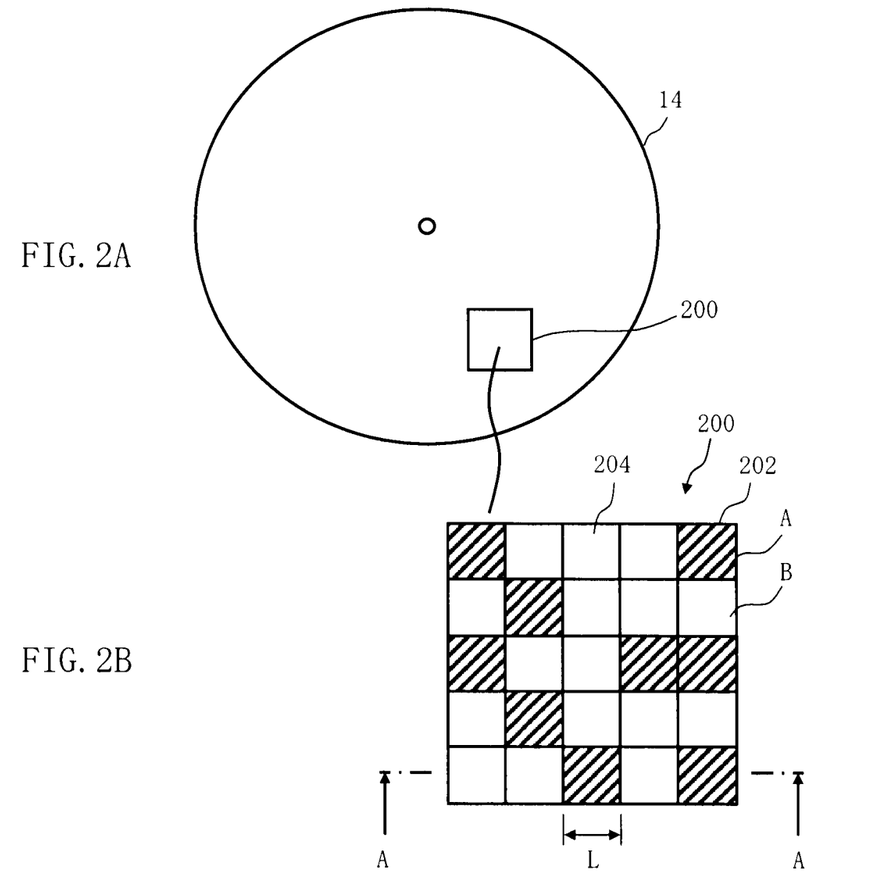
FIGS. 2A to 2C are conceptual diagrams showing the configuration of a rotating phase plate in the first embodiment.
Figure 2C:
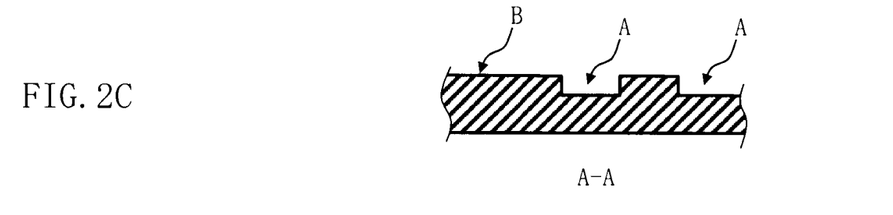

FIGS. 2A to 2C are conceptual diagrams showing the configuration of a rotating phase plate in the first embodiment. If a region 200 of the rotating phase plate 14 shown in FIG. 2A is enlarged, as shown in FIG. 2B, a plurality of step regions 202 (region A) that change the phase of a passing light beam is randomly arranged on the rotating phase plate 14. In the step region 202, as shown in FIG. 2C, steps are formed with a depth equal to or less than the wavelength being dug down from the surface of the rotating phase plate 14. In other words, steps of heights equal to or less than the wavelength are formed. Thus, non-step regions 204 (region B) having no step are also randomly arranged. The depth of the region A may be any size that leaves a depth capable of shifting the phase of a light beam by, for example, $\lambda/4$, $\lambda/2$, or $3\lambda/4$ by the light beam being passed. The rotating phase plate 14 is driven to rotate by a motor (not shown) or the like. By passing a light beam through the rotating phase plate 14 rotating at high speed, the light beam can be passed through the region A or the region B with substantially the same probability. Thus, light beams of respective phases can be formed with substantially the same probability. The step region 202 is shown in a case when the maximum dimension of outside dimensions of length and width in the direction on the surface of the rotating phase plate 14 perpendicular to the optical axis of the light beam is formed by a dimension L. In the example of FIG. 2, a case when the step region 202 is formed as a quadrangle, for example, a rectangle like a square or oblong is shown. The regions A, B that change the phase are formed, for example, as a rectangle such as a square and oblong when viewed from the front side of the rotating phase plate 14. In other words, the shape of the regions A, B on the surface perpendicular to the direction of the optical axis is formed as, for example, a rectangle such as a square and oblong. The regions A, B may have any other quadrangular shape. For example, the regions A, B may be formed as a parallelogram or a trapezoid (including a rhombus).

Figure 3:
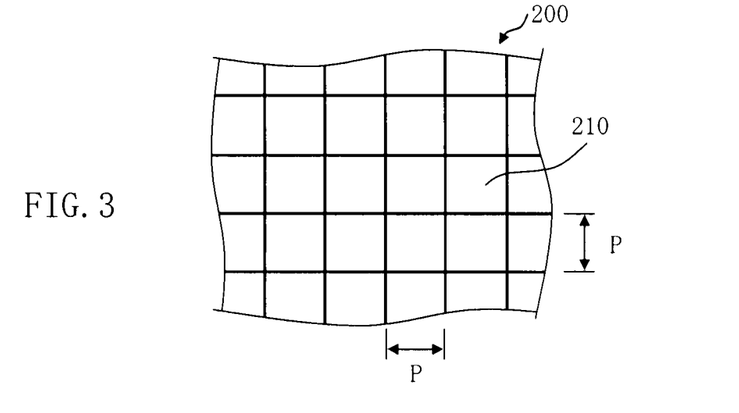
FIG. 3 is a conceptual diagram showing the configuration of an integrator in the first embodiment.

FIG. 3 is a conceptual diagram showing the configuration of an integrator in the first embodiment. In FIG. 3, a plurality of lenses 210 is arranged as an array in the integrator 20. The plurality of lenses 210 is arranged in a pitch P.

If combinations of a light beam of a plurality of phases occur with the same probability, coherence can totally be eliminated by synthesizing such combinations. For example, if two phases (0, n) are represented by three light beams a, b, c, four combinations $(0, 0, 0), (\pi, 0, \pi), (0, \pi, 0), (\pi, \pi, 0)$ can be assumed. If these four combinations occur with the same probability, coherence can totally be eliminated. For the total elimination, it is necessary that not only a case when adjacent light beams are in the same phase like the combination (0, 0, 0), $(\pi, 0, \pi)$, or $(\pi, \pi, 0)$ be present, but also a case when adjacent light beams are always in different phases like the combination $(0, \pi, 0)$ be present. However, if the widths of all light beams are larger than the pitch of the lenses 210 when the light beams enter the integrator 20 after the phase thereof is changed to one of the phases through the passage of the rotating phase plate 14, every light beam enters the integrator 20 while extending over a plurality of the lenses 210. Thus, even if the phases are shifted, light beams of the same phase may be output from the plurality of adjacent lenses 210 when the light beams are output from the integrator 20. This makes it difficult to cause a case when adjacent light beams always have different phases.

Thus, in the first embodiment, a location where the width of a light beam becomes equal to or less than the pitch of the lenses 210 when the light beam enters the integrator 20 after the phase thereof is changed to one of the phases through the passage of the rotating phase plate 14 is formed on purpose. In other words, the rotating phase plate 14 is configured so that a case when all light beams having passed through the region A enter one lens 210 is present. Similarly, the rotating phase plate 14 is configured so that a case when all light beams having passed through the region B enter one lens 210 is present. Accordingly, combinations of light of a plurality of phases output from the integrator 20 can be caused with substantially the same probability.

Thus, in the first embodiment, the relationship between the step regions 202 and the lenses 210 is specified, or "configured" so that a portion in which the product of the maximum size L of the plurality of step regions 202 and the optical magnification M from the rotating phase plate 14 to the plane of incidence of the integrator 20 is equal to or less than the arrangement pitch P of the plurality of lenses 210 of the integrator 20 and a portion in which the product is larger than the arrangement pitch P are mixed. Then, the rotating phase plate 14 and the integrator 20 that satisfy the above relationship are used. Accordingly, a case when all light beams having passed through the step regions 202 enter one of the plurality of lenses 210 of the integrator 20 can be created. Therefore, a case when light beams having passed through the adjacent lenses 210 always have different phases can be generated.

With the above configuration, combinations of light of a plurality of phases output from the integrator 20 can be caused with ever closer probabilities. As a result, coherence can be eliminated more than in the past, along with equalization of the intensity distribution.

The shape of the regions A, B of different steps of the rotating phase plate 14 is not limited to the rectangle shown in FIG. 2.

Figure 4:
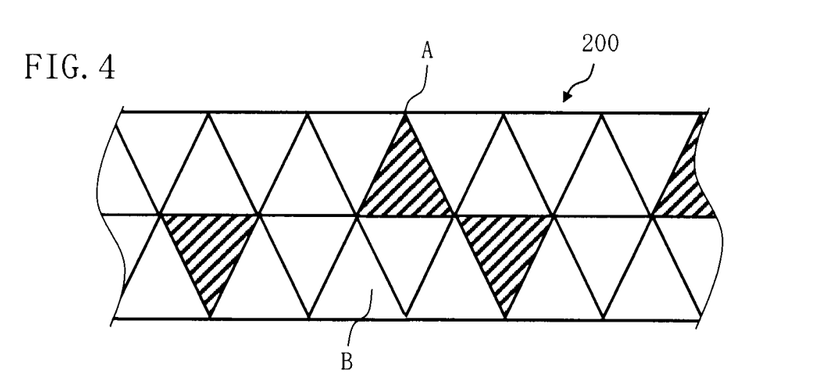
FIG. 4 is a conceptual diagram showing an example of the shape of a step region of the rotating phase plate in the first embodiment.

FIG. 4 is a conceptual diagram showing an example of the shape of a step region of the rotating phase plate in the first embodiment. As shown in FIG. 4, the shape of the regions A, B that change the phase may be a triangle, for example, an isosceles triangle. Arranging the regions A, B randomly is the same as in FIG. 2B. In this case, the maximum dimension of outside dimensions of the base and the height of the isosceles triangle only needs to be replaced with the above dimension L.

Figure 5:
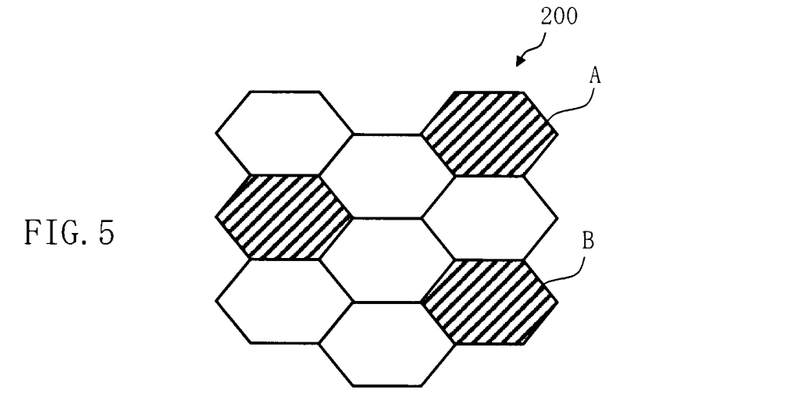
FIG. 5 is a conceptual diagram showing another example of the shape of the step region of the rotating phase plate in the first embodiment.

FIG. 5 is a conceptual diagram showing another example of the shape of the step region of the rotating phase plate in the first embodiment. As shown in FIG. 5, the shape of the regions A, B that change the phase may be a hexagon. Arranging the regions A, B randomly is the same as in FIG. 2B. The maximum dimension of vertical, horizontal, and diagonal outside dimensions of the hexagon only needs to be replaced with the above dimension L.

Figure 6A:
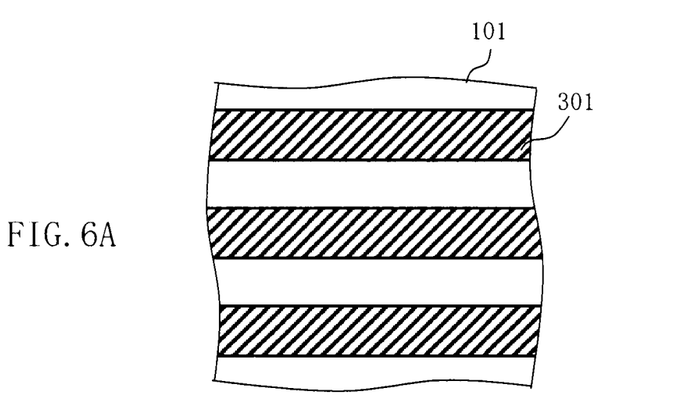
FIGS. 6A and 6B are diagrams illustrating an effect of an illuminating apparatus in the first embodiment.
Figure 6B:
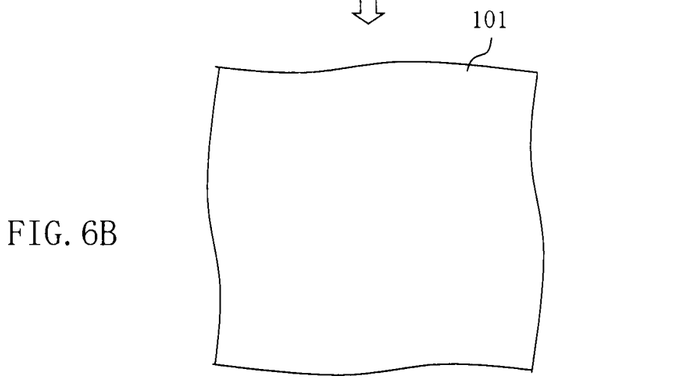

FIGS. 6A and 6B are diagrams illustrating an effect of an illuminating apparatus in the first embodiment. When every light beam enters while extending over the adjacent lenses 210, as shown in FIG. 6A, interference fringes 301 remain on the surface of an object. If, like the first embodiment, a case when light beams enter while not extending over the adjacent lenses 210 is added, by contrast, as shown in FIG. 6B, interference fringes on the surface of an object can be avoided being left. According to the first embodiment, as described above, more coherence of coherent light can be eliminated.

By using the illuminating optical system 170 and the light source 103 configured as described above, a pattern inspection apparatus that carries out a pattern inspection will be described below.

Figure 7:
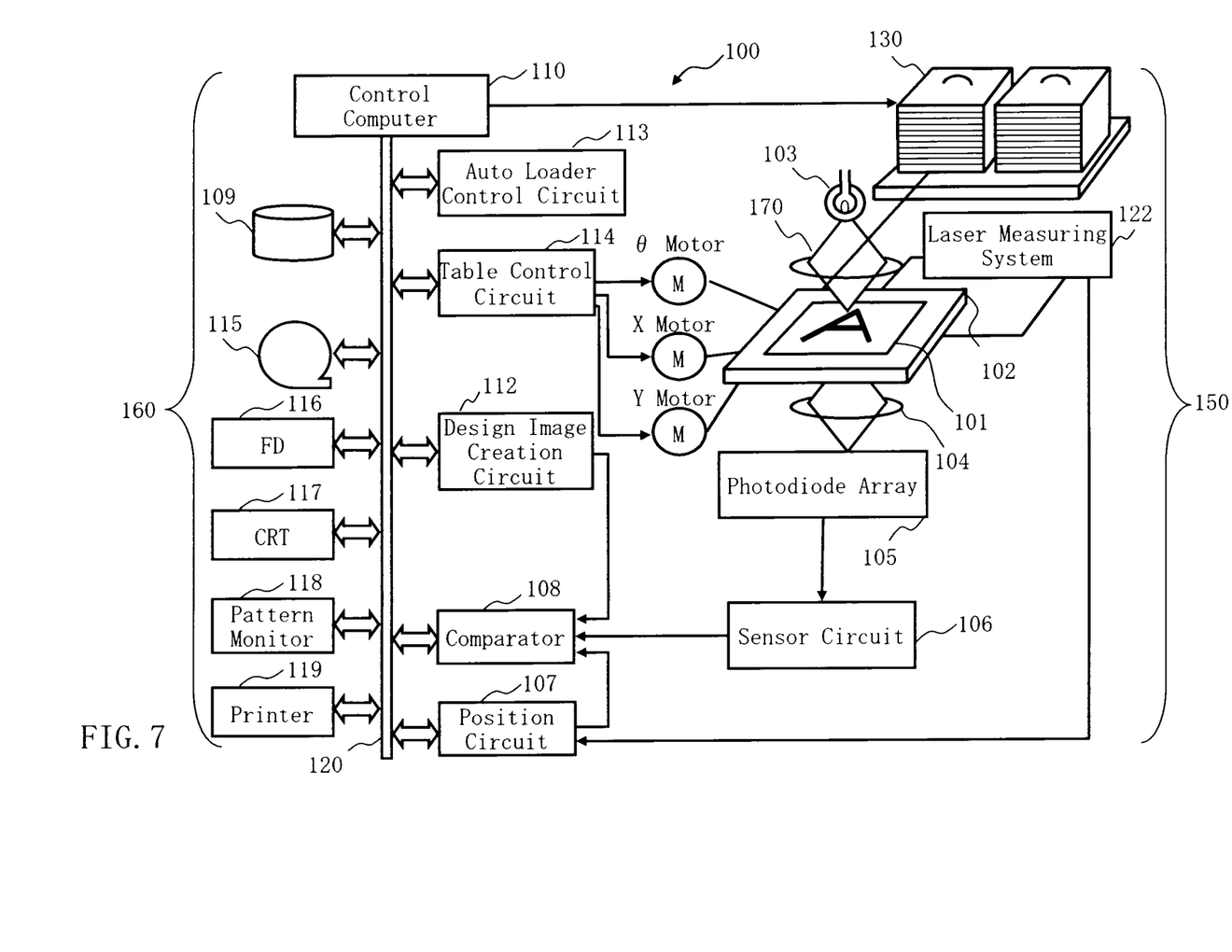
FIG. 7 is a conceptual diagram showing the configuration of a pattern inspection apparatus in the first embodiment.

FIG. 7 is a conceptual diagram showing the configuration of a pattern inspection apparatus in the first embodiment. In FIG. 7, a pattern inspection apparatus 100 that inspects a target object which is a substrate such as a mask, includes the light source 103, the illuminating optical system 170, an optical image acquisition unit 150, and a control circuit 160. The optical image acquisition unit 150 includes an XYθ table 102, an enlarged optical system 104, a photodiode array 105, a sensor circuit 106, a laser measuring system 122, and an auto loader 130. In the control circuit 160, a control computer 110 to be a computer is connected to a bus 120 to be a data transmission path, a position circuit 107, a comparator 108 to be an example of a comparing unit, a design image creation circuit 112, an auto loader control circuit 113, a table control circuit 114, a magnetic disk drive 109 to be an example of a storage apparatus, a magnetic tape apparatus 115, a flexible disk apparatus (FD) 116, a CRT 117, a pattern monitor 118, and a printer 119. The XYθ table 102 is driven by an X-axis motor, Y-axis motor, and θ-axis motor. In FIG. 7, only constituent elements necessary to describe the first embodiment are shown. The pattern inspection apparatus 100 generally may include other necessary configurations as a matter of course.

Before starting the inspection, the photomask 101 to be a pattern-formed target object to be inspected is loaded onto the XYθ table 102 provided movably in the horizontal direction and the rotation direction by motors of each of the XYθ axes by the auto loader 130 controlled by the auto loader control circuit 113 and then mounted on the XYθ table 102. Information (design pattern data) of a design pattern used for pattern formation of the photomask 101 is input into the pattern inspection apparatus 100 from outside the apparatus and stored in the magnetic disk drive 109 as an example of the storage apparatus (storage unit).

The XYθ table 102 is driven by the table control circuit 114 under the control of the control computer 110.

The XYθ table 102 is movable by a drive system like a 3-axis (X-Y-θ) motor that drives the XYθ table 102 in the X direction, Y direction and θ direction. A step motor, for example, can be used as these X motor, Y motor, and θ motor. Then, the movement position of the XYθ table 102 is measured by the laser measuring system 122 and supplied to the position circuit 107. The photomask 101 on the XYθ table 102 is automatically transported by the auto loader 130 driven by the auto loader control circuit 113 and automatically ejected after the inspection is completed. The enlarged optical system 104 is driven by, for example, a piezoelectric-crystal element and an image is focused on the photodiode array 105.

Figure 8:
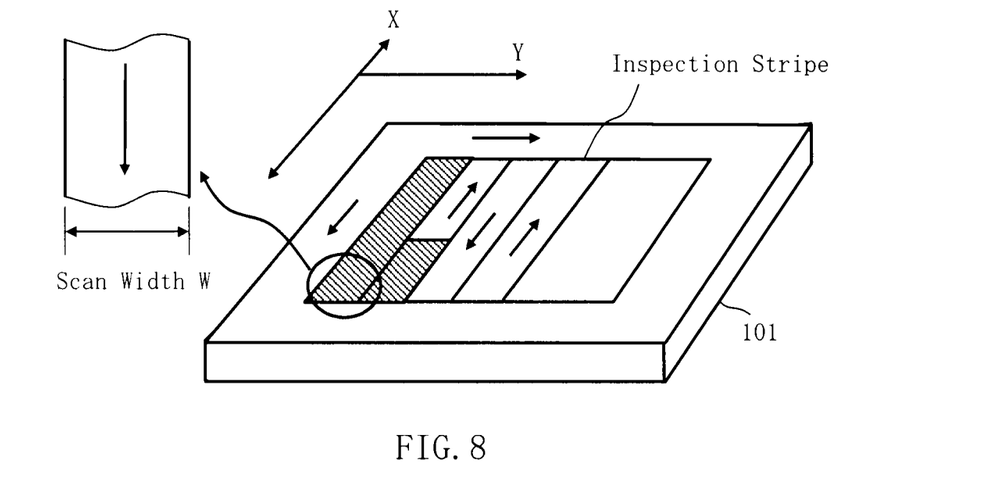
FIG. 8 is a diagram illustrating a procedure for acquiring an optical image in the first embodiment.

FIG. 8 is a diagram illustrating a procedure for acquiring an optical image in the first embodiment. The region to be inspected is virtually divided, as shown in FIG. 8, into a plurality of inspection stripes in a thin strip shape of a scan width W, for example, in the Y direction. The operation of the XYθ table 102 is controlled so that each divided inspection stripe is further scanned continuously and an optical image is acquired while moving in the X direction. An image of the scan width W as shown in FIG. 8 is continuously input into the photodiode array 105. Then, after an image in a first inspection stripe is acquired, similarly an image in a second inspection stripe of the scan width W is continuously input while moving in the opposite direction this time. Then, when an image in a third inspection stripe is acquired, the image is acquired by moving in a direction opposite to the direction to acquire the image in the second inspection stripe, that is, by moving in the direction to acquire the image in the first inspection stripe. Thus, a wasteful processing time can be reduced by continuously acquiring images. The forward (FWD)-backward (BWD) technique is used here, but the forward (FWD)-forward (FWD) technique may also be used.

A pattern formed on the photomask 101 is irradiated with light by the light source 103 arranged above the XYθ table 102. The photomask 101 is irradiated with coherent light irradiated from the light source 103 via the illuminating optical system 170 described above. The light having passed through the photomask 101 after irradiation enters the photodiode array 105 while forming an optical image thereon via the enlarged optical system 104. The image of a pattern formed on the photodiode array 105 is photoelectrically converted by the photodiode array 105 and further A/D (analog-digital) converted by the sensor circuit 106. In the photodiode array 105, sensors, for example, TDI (time delay integrator) sensor are set up. In the manner described above, the optical image acquisition unit 150 acquires optical image data (stripe data) for each inspection stripe of the target object to be inspected.

Measured data (optical image data) of each inspection stripe output from the sensor circuit 106 is output to the comparator 108 sequentially for each inspection stripe together with data output from the position circuit 107 to indicate the position of the photomask 101 on the XYθ table 102. Measured data is, for example, 8-bit unsigned data for each pixel and represents the level of brightness of each pixel by 0 to 255. An inspecting optical system of high magnification is constructed from the light source 103, the illuminating optical system 170, the enlarged optical system 104, the photodiode array 105, and the sensor circuit 106.

The design image creation circuit 112 (reference image creation unit) reads design pattern data from the magnetic disk drive 109 through the control computer 110 for each predetermined region and converts (expansion processing) the read design pattern data of the photomask 101 into design image data (reference image data) which is binary or multi-valued image data. The predetermined region may be a region (area) of an image corresponding to the optical image to be compared. The created reference image data is output to the comparator 108.

Figures constituting patterns defined in design pattern data are based on rectangles and triangles as basic figures and the design pattern data stores figure data that defines the shape, size, position and the like of each pattern figure by information like, for example, coordinates (x, y) of the figure in the reference position, lengths of sides, and figure code serving as an identifier to distinguish the type of figure such as the rectangle and triangle.

If such figure data is input into the design image creation circuit 112, the design image creation circuit 112 expands the figure data into data for each figure to interpret figure code indicating the figure shape of the figure data and figure dimensions. Then, the design image creation circuit 112 expands binary or multi-valued image data as a pattern arranged within a square in units of grid of predetermined quantization dimensions. Then, the expanded image data is stored in a pattern memory (not shown) in the circuit or the magnetic disk drive 109. In other words, the design image creation circuit 112 reads design pattern data, operates the occupation rate occupied by figures in a design pattern for each square created by virtually dividing the inspection region into the squares in units of predetermined dimensions, and outputs n-bit occupation rate data to the pattern memory (not shown) or the magnetic disk drive 109. For example, one square may preferably be set as a pixel. If the resolution of $1/2^8$ (=$1/256$) is provided to each pixel, the occupation rate in a pixel is operated by assigning a small region of $1/256$ to only a region of figures arranged in the pixel. Then, the expanded image data is stored in the pattern memory or the magnetic disk drive 109 as image data in units of area defined as 8-bit occupation rate data for each pixel.

Then, data processing (image processing) is performed on the expanded image data to perform suitable filter processing. Optical image data (measured data) is in a filter-acted state by resolution properties of the enlarged optical system 104, the aperture effect of the photodiode array 105 and the like, in other words, a continuously changing analog state. Thus, expanded image data, which is image data on the design side in which image intensity (gray-scale value) is a digital value, can be fitted to measured data by also performing filter processing according to a predetermined model thereon. For example, the filter processing such as resize processing that performs enlargement or reduction processing, corner rounding processing, and blurring processing is performed. In this manner, design images are created.

Then, the comparator 108 reads optical image data for each stripe and cuts out the optical image data so that the optical image data becomes an image of a region of the same size as the size of reference data. Then, the comparator 108 compares the corresponding optical image data and reference data after positioning pixel by pixel under predetermined judgment conditions. Such an inspection technique is a die-to-database inspection. Then, a comparison result is output. The comparison result only needs to be output from the magnetic disk drive 109, the magnetic tape apparatus 115, the flexible disk apparatus (FD) 116, the CRT 117, the pattern monitor 118, or the printer 119.

Figure 9:
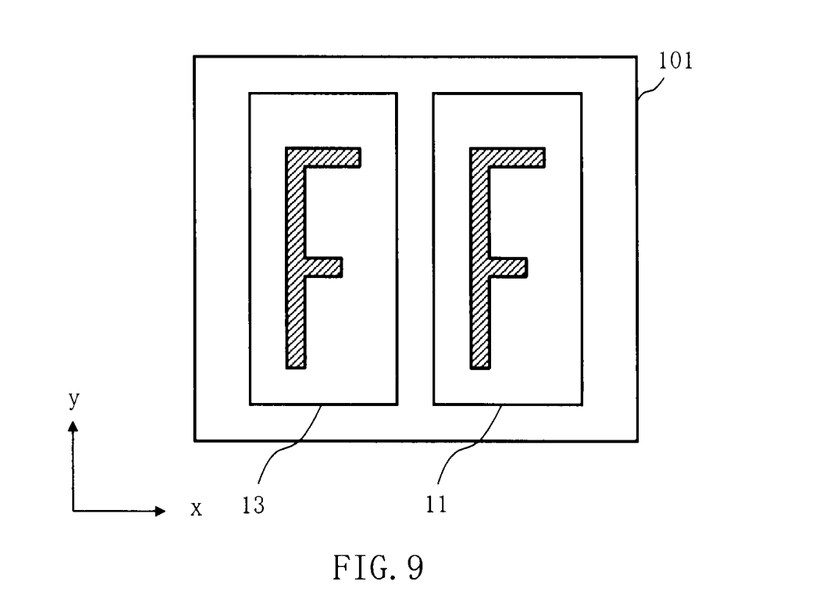
FIG. 9 is a conceptual diagram showing an example of a photomask in the first embodiment and a formed pattern.

FIG. 9 is a conceptual diagram showing an example of a photomask in the first embodiment and a formed pattern. In FIG. 9, a plurality of pattern regions 11, 13 (regions to be inspected) written with the same design pattern is formed on the photomask 101. The whole region including the two pattern regions 11, 13 is virtually divided into the plurality of inspection stripes shown in FIG. 8. Then, the optical image data (measured data) is acquired for each inspection stripe by the optical image acquisition unit 150. Thus, measured data of one inspection stripe contains an image of both the pattern regions 11, 13. A die-to-die inspection may be carried out by setting an image of one of the regions 11, 13 as an image to be inspected and the other as a reference image.

According to the present embodiment, as described above, more coherence of coherent light can be eliminated. If illuminating light from which such coherence is eliminated is used as the illuminating light of pattern inspection, the resolution is improved so that more precise inspection can be carried out.

Second Embodiment

The first embodiment shows an example in which the optical magnification is changed from the rotating phase plate to the integrator, but is not limited to such an example.

Figure 10:
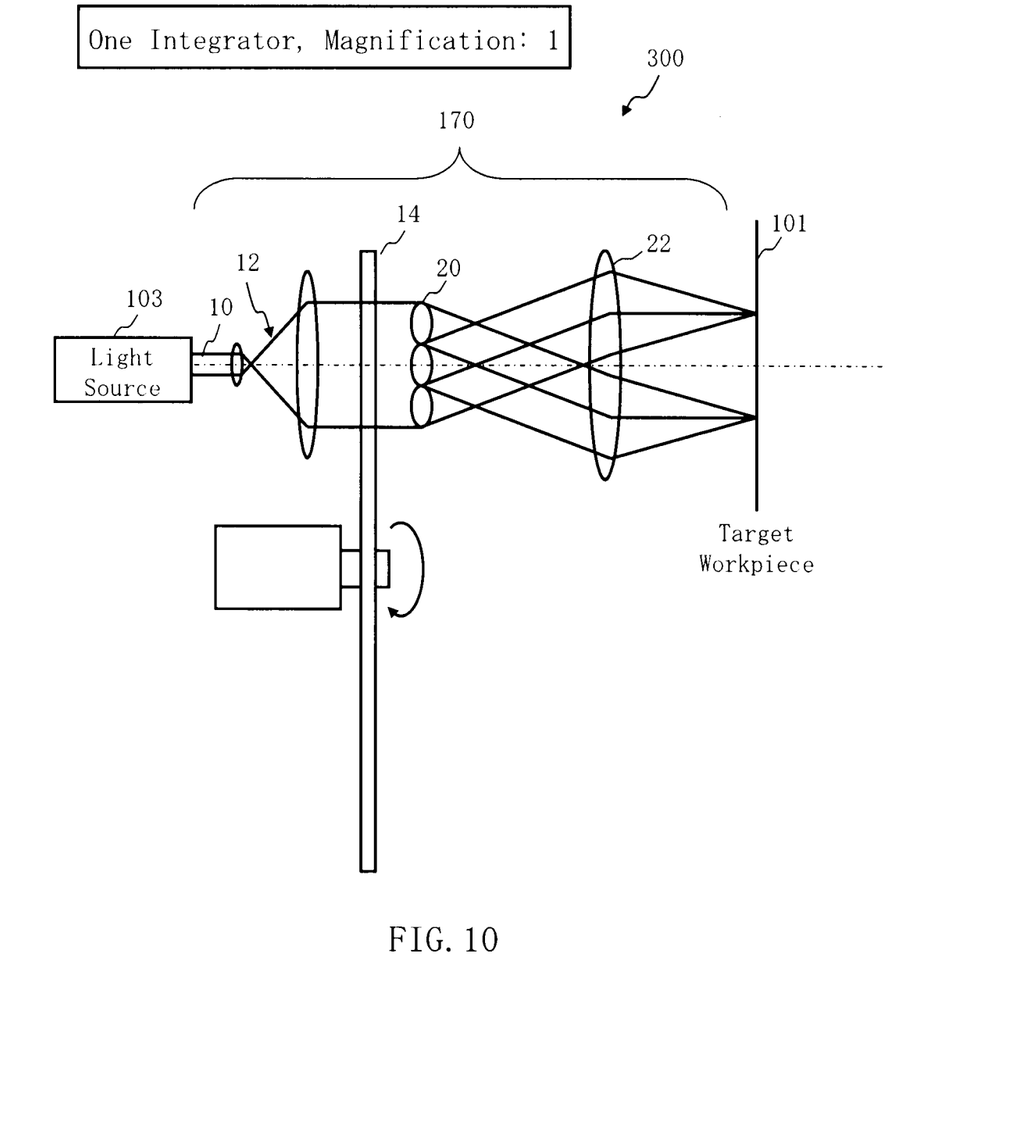
FIG. 10 is a conceptual diagram showing the configuration of an illuminating apparatus according to a second embodiment.

FIG. 10 is a conceptual diagram showing the configuration of an illuminating apparatus according to a second embodiment. FIG. 10 is the same as FIG. 1 except that the relay lenses 16, 18 between the rotating phase plate 14 and the integrator 20 are omitted. The configuration of the pattern inspection apparatus 100 is also the same as in FIG. 7. Content not specifically mentioned below is the same as in the first embodiment.

In the second embodiment, the optical magnification between the rotating phase plate 14 and the plane of incidence of the integrator 20 remains 1. In the above configuration, the relationship between the step regions 202 and the lenses 210 is specified, "configured" so that a portion in which the maximum size L of the plurality of step regions 202 is equal to or less than the arrangement pitch P of the plurality of lenses 210 of the integrator 20 and a portion in which the maximum size L is larger than the arrangement pitch P are mixed. Then, the rotating phase plate 14 and the integrator 20 that satisfy the above relationship are used. Accordingly, a case when all light beams having passed through the step regions 202 enter one of the plurality of lenses 210 of the integrator 20 can be created. Therefore, a case when light beams having passed through the adjacent lenses 210 always have different phases can be caused.

With the above configuration, combinations of light of a plurality of phases output from the integrator 20 can be caused with ever closer probabilities. As a result, coherence can be eliminated more than in the past, along with equalization of the intensity distribution.

Third Embodiment

The first and second embodiments show the configuration in which one integrator is used, but are not limited to such a configuration.

Figure 11:
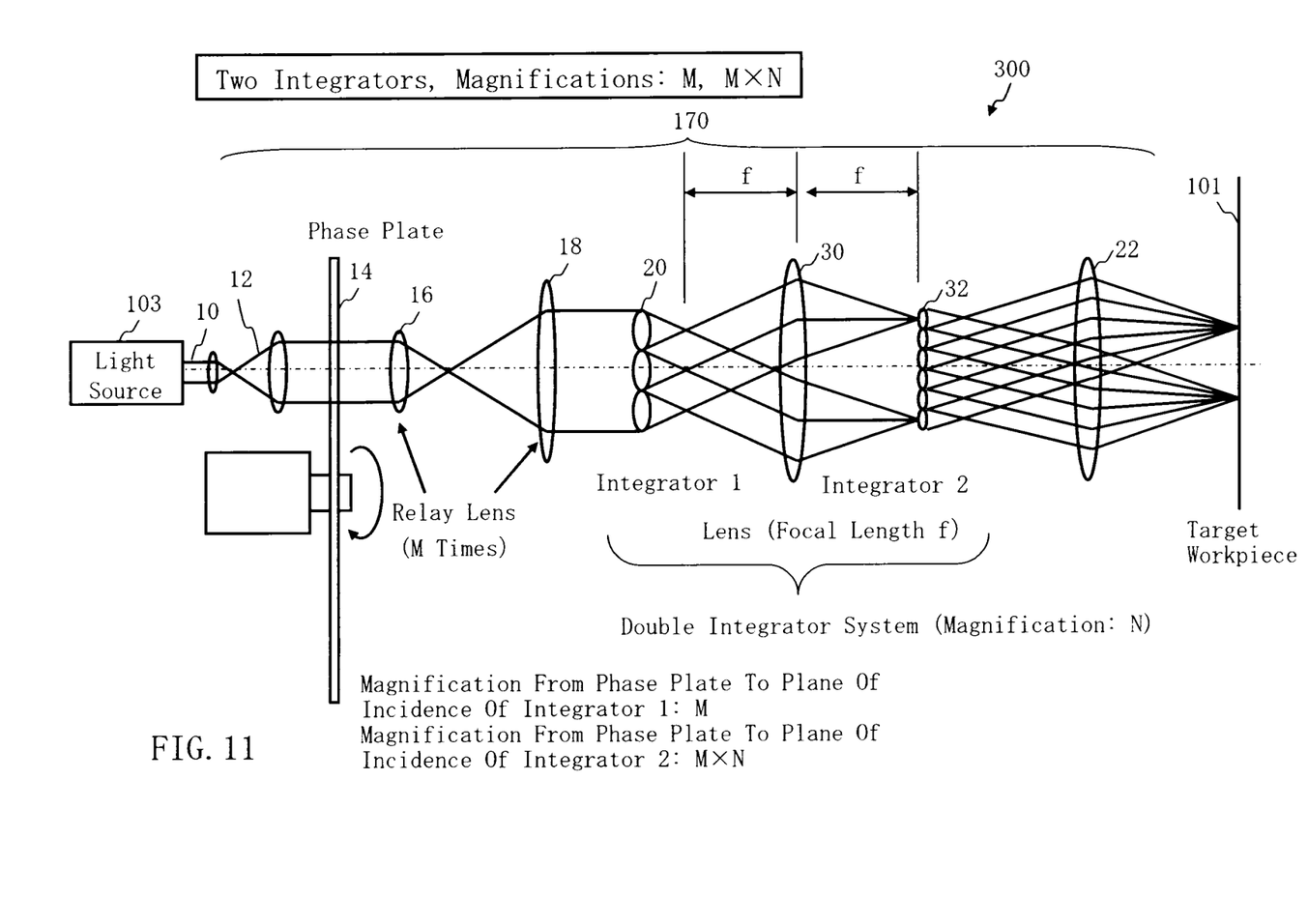
FIG. 11 is a conceptual diagram showing the configuration of an illuminating apparatus according to a third embodiment.

FIG. 11 is a conceptual diagram showing the configuration of an illuminating apparatus according to a third embodiment. FIG. 11 is the same as FIG. 1 except that a lens 30 and an integrator 32 are added to between the integrator 20 and the condenser lens 22. The configuration of the pattern inspection apparatus 100 is also the same as in FIG. 7. Content not specifically mentioned below is the same as in the first embodiment.

In the third embodiment, a plurality of integrators is arranged. Here, a case when the two integrators 20, 32 are arranged is shown. The number of integrators may be three or more. The integrators 20, 32 may have different pitches or the same pitch of the plurality of lenses 210 that are arranged as an array. In this case, the pitch of the plurality of lenses 210 of the integrator 20 is set to P1 and the pitch of the plurality of lenses 210 of the integrator 32 is set to P2. The arrangement positions of the integrators 20, 32 are different and thus, the optical magnification from the rotating phase plate 14 to the plane of incidence of each integrator is different. In this case, the optical magnification from the rotating phase plate 14 to the plane of incidence of the integrator 20 is set to M and the optical magnification from the integrator 20 to the integrator 32 is set to N. In other words, the optical magnification from the rotating phase plate 14 to the plane of incidence of the integrator 32 is set to M×N. The example in FIG. 11 shows a case when the two integrators 20, 32 are arranged across the lens 30 with a focal length f. The lens 30 and the two integrators 20, 32 are arranged so that the focal length to each integrator becomes f.

In the third embodiment, even if the relationship between the rotating phase plate 14 and the integrator 20 as, for example, in the first embodiment is maintained, when a light beam subsequently passes through the integrator 32, every light beam enters the integrator 32 while extending over adjacent lenses if the width of the light beam is larger than the pitch of the lens of the integrator 32. This makes it difficult to cause a case when adjacent light beams always have different phases.

Thus, in the third embodiment, a location where the width of a light beam becomes equal to or less than the pitch of the lenses 210 when the light beam enters the integrator 20 after the phase thereof is changed to one of the phases through the passage of the rotating phase plate 14 is formed on purpose. Similarly, a location where the width of light beams becomes equal to or less than the pitch of the lenses 210 of the integrator 32 when the light beams in which different phases are maintained between adjacent lenses by passing through one of the lenses 210 of the integrator 20 enter the integrator 32 is formed on purpose. In other words, the rotating phase plate 14 is configured so that a case when all light beams having passed through the region A enters one lens 210 of the integrator 20 and one lens 210 of the integrator 32 is present. Similarly, the rotating phase plate 14 is configured so that a case when all light beams having passed through the region B enters one lens 210 of the integrator 20 and one lens 210 of the integrator 32 is present. Accordingly, combinations of light of a plurality of phases output from the plurality of the integrators 20, 32 can be caused with substantially the same probability.

Thus, in the third embodiment, the relationship between the step regions 202 and the lenses 210 of the integrator 20 is specified, "configured" so that a portion in which the product of the maximum size L of the plurality of step regions 202 and the optical magnification M from the rotating phase plate 14 to the plane of incidence of the integrator 20 is equal to or less than the arrangement pitch P1 of the plurality of lenses 210 of the integrator 20 and a portion in which the product is larger than the arrangement pitch P1 are mixed. Similarly, the relationship between the step regions 202 and the lenses 210 of the integrator 32 is specified, "configured" so that a portion in which the product of the maximum size L of the plurality of step regions 202 and the optical magnification M×N from the rotating phase plate 14 to the integrator 32 is equal to or less than the arrangement pitch P2 of the plurality of lenses 210 of the integrator 20 and a portion in which the product is larger than the arrangement pitch P2 are mixed. Then, the rotating phase plate 14 and the integrators 20, 32 that satisfy the above relationship are used. Accordingly, a case when all light beams having passed through the step regions 202 enter one of the plurality of lenses 210 of each of the integrators 20, 32 can be created. Therefore, a case when light beams having passed through the adjacent lenses 210 always have different phases can be caused.

With the above configuration, combinations of light of a plurality of phases output from the plurality of integrators 20, 32 can be caused with ever closer probabilities. As a result, coherence can be eliminated more than in the past, along with equalization of the intensity distribution.

Figure 12:
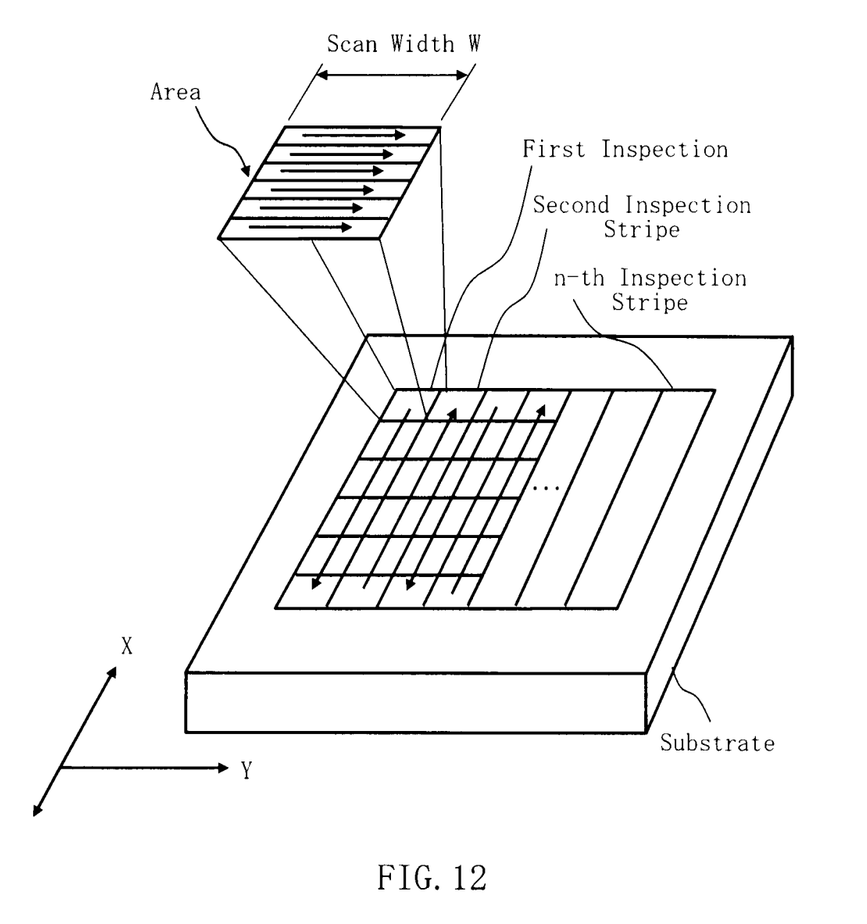
FIG. 12 is a diagram illustrating another technique for acquiring an optical image.

FIG. 12 is a diagram illustrating another technique for acquiring an optical image. In the configuration in FIG. 7 or the like, the photodiode array 105 in which pixels corresponding to the scan width W are entered at the same time is used, but the embodiments are not limited to such an example. As shown in FIG. 12, it is possible to use a technique to acquire a two-dimensional image for each area of a predetermined size by scanning in the Y direction with a laser beam using a laser scan optical apparatus (not shown) to detect transmitted light or reflected light each time movement of a constant pitch is detected by a laser interferometer while sending the XYθ table 102 at a constant speed in the X direction.

In the above description, a " . . . unit", a " . . . circuit", or a " . . . process" can be configured by a program than can be run on a computer. Alternatively, instead of only programs to be software, hardware and software may be combined to embody a unit. Alternatively, firmware may also be combined. If a unit is configured by a program, the program is recorded in a recording medium such as the magnetic disk drive 109, the magnetic tape apparatus 115, the FD 116, and a read only memory (ROM). When an arithmetic control unit is configured, the position circuit 107, the comparator 108, the design image creation circuit 112, the auto loader control circuit 113, and the table control circuit 114 may be configured by an electric circuit or realized by software that can be processed by the control computer 110. Alternatively, an electric circuit and software may be combined to realize such a unit.

The embodiments have been described with reference to the concrete examples. However, the present invention is not limited to the concrete examples. In the embodiments, for example, an optical system of transmission type using transmitted light is used, but an optical system using reflected light, or transmitted light and reflected light at the same time may be configured.

Although parts such as an apparatus configuration and a control method which are not directly required for the explanation of the present invention are not described, a required apparatus configuration or a required control method can be arbitrarily selected and used.

In addition, all pattern inspection apparatuses and all pattern inspection methods which include the elements of the present invention and can be obtained by arbitrary change of design by a person skilled in the art are included in the spirit and scope of the invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An illuminating apparatus, comprising:
a light source configured to generate coherent light;
a rotating phase plate in which a plurality of step regions is arranged randomly and has a height equal to or less than a wavelength of the light, and configured to change a phase of a light beam from the light source by allowing the light beam to pass therethrough; and
a fly's eye lens in which a plurality of lenses is arranged like an array and configured to allow the light beam having passed through the rotating phase plate to pass,
wherein a portion in which a product of a maximum size of the plurality of step regions and an optical magnification from the rotating phase plate to a plane of incidence of the fly's eye lens is equal to or less than an arrangement pitch of the plurality of lenses, a portion in which the product is larger than the arrangement pitch of the plurality of lenses are mixed, the maximum size of the plurality of step regions is a maximum width size on a surface of each step region perpendicular to a direction of an optical axis and the surface of each step region is formed in a same shape.

2. The apparatus according to claim 1, wherein a shape of the plurality of step regions on a surface perpendicular to a direction of an optical axis is formed as a quadrangle.

3. The apparatus according to claim 1, wherein a shape of the plurality of step regions on a surface perpendicular to a direction of an optical axis is formed as a triangle.

4. The apparatus according to claim 1, wherein a shape of the plurality of step regions on a surface perpendicular to a direction of an optical axis is formed as a polygon.

5. The apparatus according to claim 1, further comprising:
a lens configured to be arranged between the rotating phase plate and the fly's eye lens and to adjust the optical magnification.

6. An illuminating apparatus, comprising:
a light source configured to generate coherent light;
a rotating phase plate in which a plurality of step regions is arranged randomly and has a height equal to or less than a wavelength of the light, and configured to change a phase of a light beam from the light source by allowing the light beam to pass therethrough; and
a fly's eye lens in which a plurality of lenses is arranged like an array and configured to allow the light beam having passed through the rotating phase plate to pass,
wherein a portion in which a maximum size of the plurality of step regions is equal to or less than an arrangement pitch of the plurality of lenses, a portion in which the maximum size is larger than the arrangement pitch of the plurality of lenses are mixed, the maximum size of the plurality of step regions is a maximum width size on a surface of each step region perpendicular to a direction of an optical axis and the surface of each step region is formed in a same shape.

7. An illuminating apparatus, comprising:
a light source configured to generate coherent light;
a rotating phase plate in which a plurality of step regions is arranged randomly and has a height equal to or less than a wavelength, and configured to change a phase of a light beam from the light source by allowing the light beam to pass therethrough; and
a plurality of fly's eye lenses in which a plurality of lenses is arranged like an array, configured to have different arrangement positions from the rotating phase plate, and configured to allow the light beam having passed through the rotating phase plate to pass,
wherein a portion in which a first product of a maximum size of the plurality of step regions and an optical magnification from the rotating phase plate to a plane of incidence of one of the fly's eye lenses is equal to or less than an arrangement pitch of the plurality of lenses of the one of the fly's eye lenses and a portion in which the first product is larger than the arrangement pitch of the plurality of lenses of the one of the fly's eye lens are mixed, and a portion in which where a second product of the maximum size of the plurality of step regions and the optical magnification from the rotating phase plate to the plane of incidence of the other of the fly's eye lenses is equal to or less than the arrangement pitch of the plurality of lenses of the other of the fly's eye lenses, a portion in which where the second product is larger than the arrangement pitch of the plurality of lenses of the other of the fly's eye lenses are mixed, the maximum size of the plurality of step regions is a maximum width size on a surface of each step region perpendicular to a direction of an optical axis and the surface of each step region is formed in a same shape.

8. The apparatus according to claim 7, further comprising:
a lens configured to be arranged between the plurality of fly's eye lenses.

9. A pattern inspection apparatus, comprising:
a light source configured to generate coherent light;
a rotating phase plate in which a plurality of step regions is arranged randomly and has a height equal to or less than a wavelength of the light, and configured to change a phase of a light beam from the light source by allowing the light beam to pass therethrough;
a fly's eye lens in which a plurality of lenses is arranged like an array and configured to allow the light beam having passed through the rotating phase plate to pass;
an optical image acquisition unit configured to acquire an optical image of a pattern by using the light beam having passed through the fly's eye lens as illuminating light and by illuminating a substrate on which the pattern is formed with the illuminating light; and
a comparing unit configured to compare the optical image and a reference image,
wherein a portion in which a product of a maximum size of the plurality of step regions and an optical magnification from the rotating phase plate to a plane of incidence of the fly's eye lens is equal to or less than an arrangement pitch of the plurality of lenses, a portion in which the product is larger than the arrangement pitch of the plurality of lenses are mixed, the maximum size of the plurality of step regions is a maximum width size on a surface of each step region perpendicular to a direction of an optical axis and the surface of each step region is formed in a same shape.

10. A method of forming illuminating light, comprising:
generating coherent light from a light source;
changing a phase of a light beam from the light source by causing a rotating phase plate that has a plurality of step regions arranged randomly and having a height equal to or less than a wavelength formed thereon to pass the light beam from the light source; and
causing a fly's eye lens in which a plurality of lenses is arranged like an array to pass the light beam having passed through the rotating phase plate,
wherein a relationship between the rotating phase plate and the fly's eye lens, is configured to mix a portion in which a product of a maximum size of the plurality of step regions and an optical magnification from the rotating phase plate to a plane of incidence of the fly's eye lens is equal to or less than an arrangement pitch of the plurality of lenses, a portion in which the product is larger than the arrangement pitch of the plurality of lenses, the maximum size of the plurality of step regions is a maximum width size on a surface of each step region perpendicular to a direction of an optical axis and the surface of each step region is formed in a same shape.

* * * * *